United States Patent [19]

Chu et al.

[11] Patent Number: 5,571,667
[45] Date of Patent: Nov. 5, 1996

[54] ELONGATED MEMBRANE FLOW-THROUGH DIAGNOSTIC DEVICE AND METHOD

[76] Inventors: Albert E. Chu, 140 Roblar Ave., Hillsborough, Calif. 94010; Peter K. Chun, 2566 Adams Ct., So., South San Francisco, Calif. 94080; Siu Chin C. Yeung, 36 Ottawa St., San Mateo, Calif. 94401

[21] Appl. No.: 89,429

[22] Filed: Jul. 8, 1993

Related U.S. Application Data

[63] Continuation of Ser. No. 958,537, Oct. 8, 1992, abandoned, which is a continuation of Ser. No. 798,346, Nov. 21, 1991, abandoned, which is a continuation of Ser. No. 358,786, May 26, 1989, abandoned, which is a continuation-in-part of Ser. No. 103,845, Oct. 1, 1987, Pat. No. 5,006,464.

[51] Int. Cl.$^6$ .................................................. C12Q 1/70
[52] U.S. Cl. ................................. 435/5; 435/6; 435/7.92; 435/7.93; 435/7.94; 435/7.95; 435/962; 435/970; 435/973; 435/974; 436/501; 436/518; 436/525; 436/809; 436/810; 422/56; 422/57; 422/58; 422/61
[58] Field of Search ............................ 435/5,7.92, 7.93, 435/7.94, 7.95, 6, 288, 6, 962, 970, 973, 974; 436/501, 518, 530, 525, 809, 810; 422/56, 57, 58, 61

[56] References Cited

U.S. PATENT DOCUMENTS

| | | | |
|---|---|---|---|
| 4,632,901 | 12/1986 | Valkirs et al. | 435/5 |
| 4,775,636 | 10/1988 | Moeremans et al. | 436/518 |
| 4,810,630 | 3/1989 | Craig et al. | 435/7.9 |
| 4,816,387 | 3/1989 | Osther | 435/5 |
| 4,912,034 | 3/1990 | Kalra et al. | 435/7 |
| 4,945,057 | 7/1990 | Temeyer et al. | 436/548 X |
| 5,006,464 | 4/1991 | Chu et al. | 435/7.1 |
| 5,026,653 | 6/1991 | Lee et al. | 436/518 |
| 5,296,467 | 3/1994 | Reutelingsperger | 514/12 |

FOREIGN PATENT DOCUMENTS

| | | | |
|---|---|---|---|
| 2099578 | 8/1982 | United Kingdom | 435/7.32 |

OTHER PUBLICATIONS

Blomberg et al. Jan. 1988, Quantication of Immuroglobulin . . . J. Chim. Microbiol 26:111–115.

*Primary Examiner*—Carol A. Spiegel
*Attorney, Agent, or Firm*—Flehr, Hohbach, Test, Albritton & Herbert

[57] ABSTRACT

An apparatus is provided for use in assays for the detection of a bindable target substance in a liquid sample. The apparatus comprises an elongate reaction membrane strip which is porous and liquid-permeable, the upper surface of the membrane strip having receptors thereon capable of binding to the target substance; an absorbent material located adjacent to the lower surface of the reaction membrane strip; and a container means for the reaction membrane strip and absorbent material, including a top wall defining a fluid port in the form of an elongate slot adjacent the membrane strip and including a fluid seal means disposed at the periphery of the fluid port defining a seal between the container top wall and reaction membrane strip. In one embodiment, the receptors on the membrane strip correspond to Western blot proteins. An assay for the detection of bindable target antibody in a liquid sample employing the apparatus is also described.

23 Claims, 3 Drawing Sheets

ELONGATED MEMBRANE FLOW-THROUGH DIAGNOSTIC DEVICE AND METHOD

This is a continuation of application Ser. No. 07/958,537, filed Oct. 8, 1992, now abandoned, which is a continuation of application Ser. No. 7/798,346, filed Nov. 21, 1991, now abandoned, which is a continuation of application Ser. No. 07/358,786, filed May 26, 1989, now abandoned, which is a continuation-in-part of Ser. No. 103,845, filed Oct. 1, 1987, issued U.S. Pat. No. 5,006,464.

TECHNICAL FIELD

The present invention relates to devices and methods for analyte assay in liquid samples. More particularly, the invention relates to devices and methods utilizing immobilized specific binding receptors for analytes in liquid samples derived from biological specimens.

BACKGROUND OF THE INVENTION

There has long been an interest in the development of assay systems which can determine the presence or amount of specific substances in samples derived from biological specimens. Over the past two decades, immunoassays, which employ naturally occurring receptors directed to specific target substances, have provided valuable diagnostic tools for detecting substances of clinical significance. There are numerous immunoassays in the prior art in which one component of an immunological pair, e.g., an antigen or antibody, is detected or measured by using the complementary partner labelled with a tag which provides a detectible signal.

In one assay technique, known as a competitive binding technique, the substance to be detected competes with a labelled reagent of the same substance for a limited number of receptor sites. For example, for the detection of an unknown amount of a selected antigen in a liquid sample, a known amount of the labelled antigen is added to the sample and then contacted with receptor antibody specific for the antigen. The amount of labelled antigen which binds to the antibody is inversely proportional to the amount of the unknown antigen in the sample.

In another assay, known as a sandwich assay, receptor antibody is bound to a solid surface and the selected antigen in the sample binds to that antibody. A second labelled antibody capable of binding to the bound antigen is then reacted with the antigen to form an immobilized reaction product. The label in the reaction product is detected as an indication of the presence of the antigen in the sample.

For the detection or measurement of an antigen using a sandwich technique, antisera have been used for many years for both the labelled antibody and for the receptor antibody on the surface. More recently, monoclonal antibodies have been used in place of the antisera in such assay. In one such system, described in Wada, et al., Clin. Chem., 28(9):1986–1966 (1982), the receptor antibody was directed to one subunit of a particular antigen, hCG, while an enzyme-labelled monoclonal antibody was directed to another subunit. In this assay, the receptor antibody is immobilized on the inside of the test tube to which the sample was added.

Reaction on a solid surface can be relatively slow because the contact between the immobilized reagent and the analyte in the sample is limited. The assay time has been reduced by immobilizing the receptor antibody within a porous membrane, exposing the antibody molecules in a three-dimensional matrix. In many such systems the liquid sample containing the target antigen is drawn through the membrane into an underlying absorbent material. One such system, disclosed for use in a competitive binding assay, is U.S. Pat. No. 3,888,629. Other systems disclosed for use in competitive or sandwich assays include U.S. Pat. Nos. 4,246,339 and 4,366,241.

It is known to immobilize an antibody onto a membrane to bind an antigen and detect it, e.g. in a sandwich assay. The sample solutions and reagents flow through the membrane into an absorbent material on the other side of the membrane. One such system is described in U.S. Pat. No. 4,632,901. However, there is no suggestion that this type of system could be utilized for the detection of protein blots.

Protein blotting is a term used to describe the transfer of electrophoretically-resolved biological protein samples to an immobilizing matrix followed by a detection. Where the biological specimen is a protein, the blot is referred to as a Western blot. The general techniques for separations of the proteins and for blotting on the immobilized phase are well known (Techniques in Molecular Microbiology, J. Walker and W. Gaastre (Eds); G. Bers and D. Garfin, Bio Techniques, Vol. 3, No. 4, pp.276–288 (1985); Journal of Immunological Methods, 100 (1987) 281–282). As described, polyacrylamide gel electrophoresis is one suitable technique for this separation. Blotting matrices are available including nitrocellulose, diazobenzyloxymethyl (DBM) and diazophenylthioether (DPT)—modified cellulose paper and ion exchange papers (e.g. diethylaminoethyl (DEAE) cellulose). Nitrocellulose is a particularly effective blotting membrane. In a typical application, the proteins migrate through the gel under the influence of an electric field. The rate of migration is dependent on the charge, size and shape of the protein. The protein in the gel is then electrophoretically transferred to a support medium such as the nitrocellulose membrane.

After the blotting process, the protein on the membrane is detected in any of the aforementioned techniques. Commonly, antibody and various labelled materials such as an enzyme conjugate or a complex of colloidal gold with antibody has been used to detect the protein. It is known that the specificity of blotting may be difficult to control to avoid nonspecific binding to the membrane. Accordingly, a variety of blocking agents have been applied to the membrane prior to addition of the sample and labelled antibody. A common effective blocking agent is the surfactant polyoxyethylene sorbitan monolaurate surfactant (TWEEN-20). Such blocking agent is usually added at a low concentration, e.g. 0.05% polyoxyethylene sorbitan monolaurate surfactant (TWEEN-20).

Strips of nitrocellulose containing electrophoretically separated HIV-1 viral protein are commercially available for the detection of antibodies in an AIDS patient's serum. In such techniques, the strips are immersed into a solution of serum sample and labelled second antibody and mechanically agitated during incubation. Wash steps are normally required between incubations. Assay procedures of this type, termed overlays, typically require several hours. Thus, the procedure is labor and apparatus intensive.

Moreover, incubating such protein containing nitrocellulose strips with continuous agitation cause elution from the membrane of substantial portions of the blotted proteins. Another problem with this overlay approach is the protein blot is surrounded by an unstirred layer of solvent which restricts diffusion in mass transport across the liquid solid interface (Nernst law). This causes the antibody to be bound more quickly than it can be replenished by diffusion from the bulk solution. Thus, the observed rate constant is slower than expected and a slower reaction occurs.

A variety of label reagents have been used for anti-HIV immuno-blotting assays. Typically, such assays use a secondary antibody for visualizing antigen-bound primary antibodies. While enzymes have been used, gold labelled secondary antibodies have also been employed.

SUMMARY OF THE INVENTION

This invention provides an assay device and method for detecting an analyte in a liquid sample, particularly a sample derived from biological specimen. The device of the present invention includes a porous reaction membrane with an immobilized receptor which is capable of directly or indirectly binding to the target substance. The device also includes a body of absorbent material located adjacent to the porous reaction membrane which is capable of absorbing the liquid sample.

The liquid sample is assayed to form a detectible reaction product on the membrane. In preferred assay embodiments, the liquid sample is biologically derived (e.g., urine or serum) and is suspected to include as the target substance, typically an antigen, antibody, or hapten capable of being bound by the receptor immobilized on the membrane.

In the detection of a selected antigen in a sandwich assay, a receptor antibody reagent (to which the antigen binds) is immobilized on the membrane. Target antigen in a fluid sample is bound to the receptor antibody. A second reagent, soluble labelled antibody capable of binding the target antigen, then reacts with the bound antigen to form a detectible reaction product on the membrane. These reactions can be simultaneous or sequential.

In the present invention, the receptor on the membrane is an antigen, preferably a protein blot, and the bindable target substance in the liquid sample comprises antibody. More specifically, a preferred antigen is an HIV viral protein.

The apparatus include an elongate fluid port with a fluid seal disposed at the periphery of the fluid port defining a seal between a container wall and reaction membrane. Preferably, the reaction membrane is a strip and the fluid seal means is a continuous rim projecting from the container wall towards the strip. A preferred membrane is nitrocellulose, more particularly, paper-backed nitrocellulose.

Another aspect of the invention is the application of a blocking solution to the reaction membrane prior to the addition of the sample. In particular, a preferred blocking solution includes between about 1% and about 2% polyoxyethylene sorbitan monolaurate surfactant (available under the tradename TWEEN-20) in combination with bovine serum albumin is particularly effective.

DESCRIPTION OF THE PREFERRED EMBODIMENT

The present invention provides an improved assay device and method for detecting an analyte or target substance in a fluid sample, particularly a sample derived from a biological specimen. More specifically, the system is useful for the detection of antibody in the serum of a patient, e.g. one suspected of having AIDS, using a protein blot of viral or recombinant HIV protein, or a portion of the same, such as ENV 9 envelope protein (GP 120 and parts of GP 41 of the HIV virus).

The device of the present invention serves the combined function of storing liquid reagents and permitting their reaction on a membrane and detecting the target substance. More specifically, it includes a porous reaction membrane containing or impregnated with an immobilized receptor, specifically antigen, which is capable of directly or indirectly binding to the target substance. The device also includes a body of absorbent material located below and supporting to the porous membrane. The device is formed into a box-like container including a top wall defining a fluid port adjacent to the receptor and including a fluid seal, preferably a rim, disposed at the periphery of the fluid port.

Figure 1:
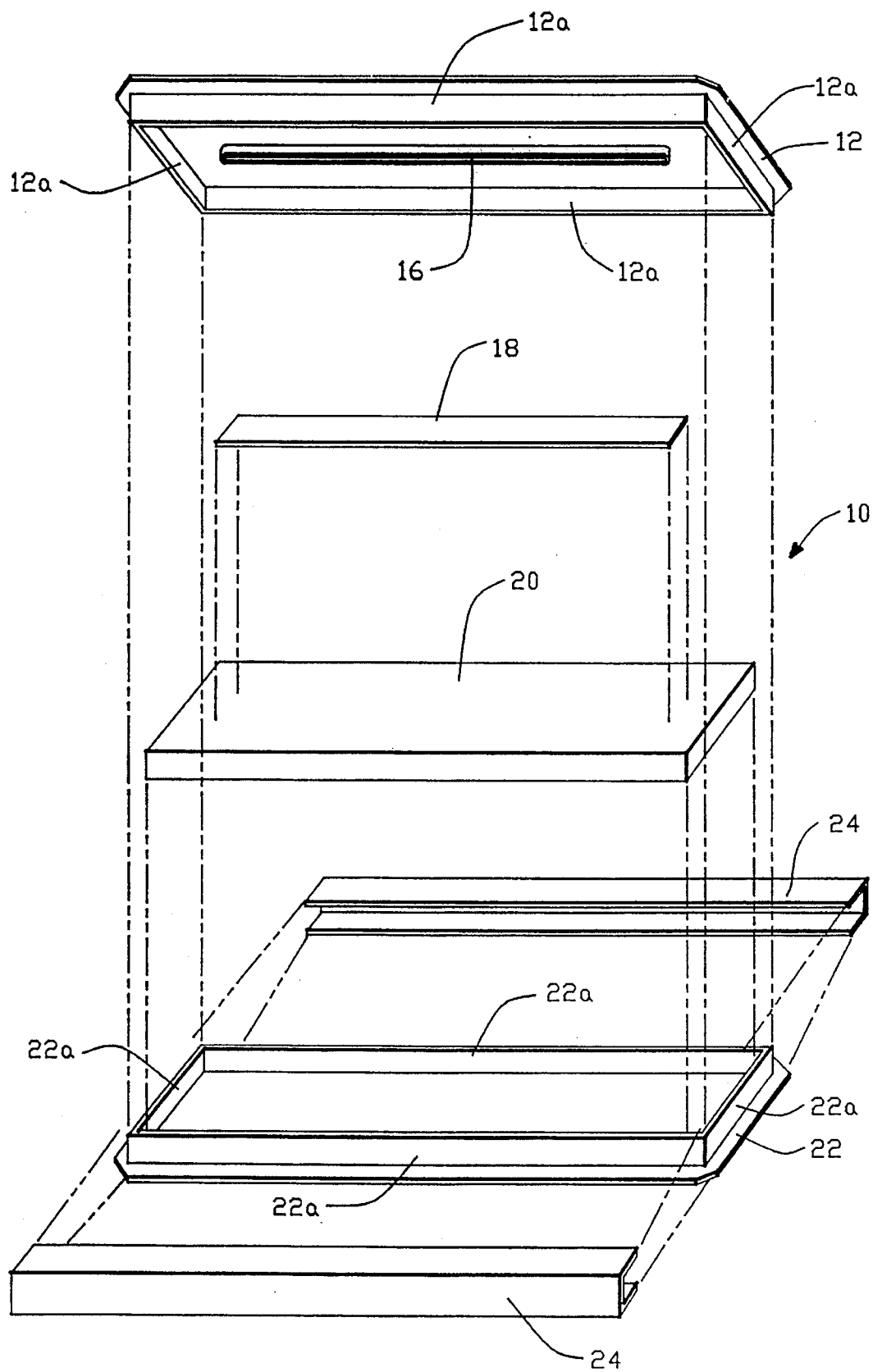
FIG. 1 is an exploded view of an assay device of the present invention.
Figure 2:
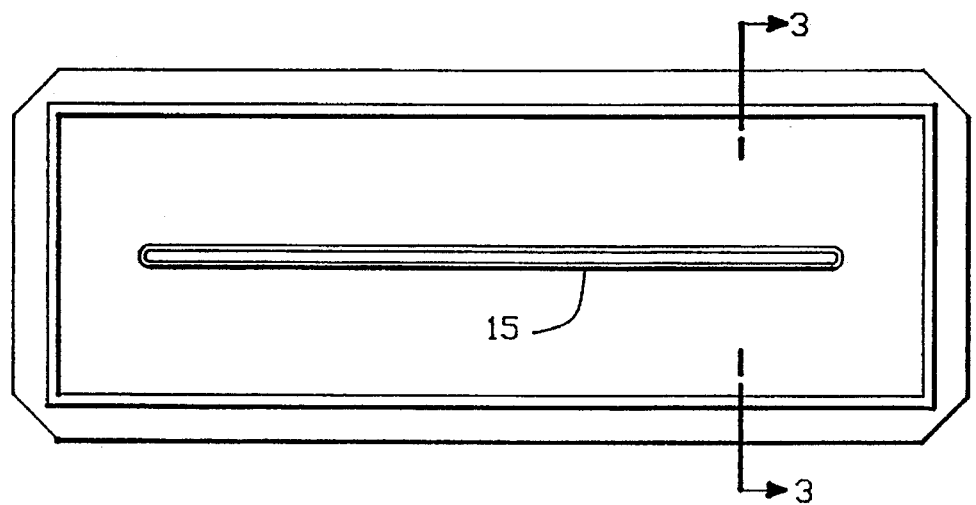
FIG. 2 is a top view of the assay device of FIG. 1.

Referring to the drawings, FIG. 1 depicts a representative assay device 10 according to the present invention which may be disposable or reusable with appropriate cleaning. While the device is illustrated in a rectangular shape, other appropriate shapes may be employed so long as it includes an appropriate port for receiving and temporarily restoring the liquid.

Figure 3:
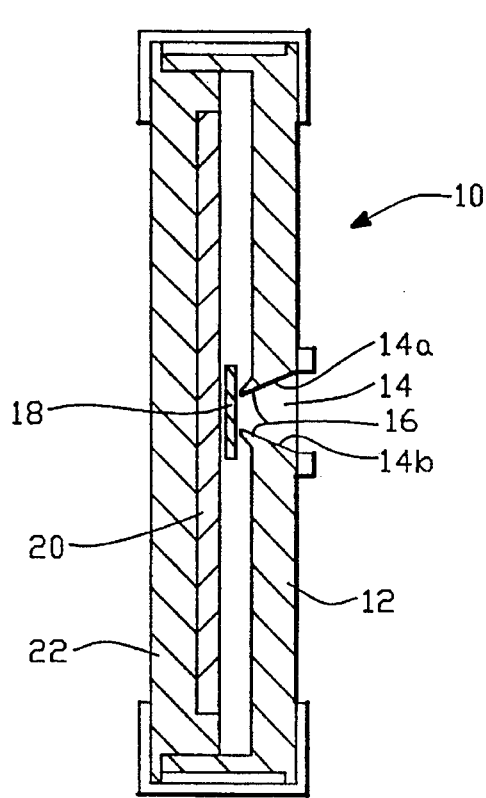
FIG. 3 is an expanded cross-sectional view of the assay device of FIG. 2 taken along the line 3—3.
Figure 4:
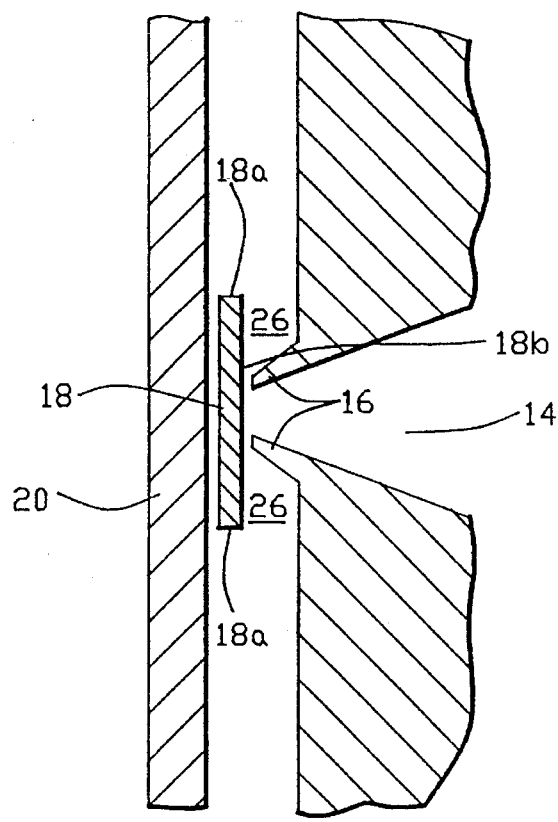
FIG. 4 is an enlarged view of a portion of the assay device of FIG. 3 illustrating the membrane and seal in detail.

Referring to FIGS. 1–4, the device of the present invention is illustrated in a form for ready assembly and disassembly. The device generally, designated by the number 10, includes a top wall 12 with a fluid port 14, best illustrated in FIGS. 3 and 4, is defined by parallel elongate side walls 14a and 14b which slope inwardly from the top to the bottom of the top wall. An upwardly projecting rim 15 is provided at the periphery of the port to contain any liquid applied to port 14 in excess of a volume which would be contained in that portion of port 14 at the level of the top wall.

Sealing means in the form of a continuous rim 16 of downwardly projecting walls 16 provided on the bottom side of top wall 12. The sealing means is disposed at the periphery of port 14 and defines a seal between the bottom of container top wall 12 and reaction membrane 18 as described below. As illustrated, such sealing means is in the form of an integral continuous rim 16 extending around the outlet of port 14. If desired, other sealing means may be employed so long as liquid flowing through port 14 continues to flow through the membrane and into absorbent material body 20 without leaking around the sealing means.

As illustrated in FIGS. 1 and 3, the device also includes a bottom wall 22 with perpendicular upwardly projecting side wall 22a defining an enclosure for absorbent material 20. Side walls 12a of top wall 12 fit over upwardly projecting side walls 22a in close tolerance. Top wall 12 and bottom wall 22 form in combination a box-like enclosure sealed against liquid except through port 14.

Clamping means is provided as a safety measure to retain top wall 12 and bottom wall 22 in contact with each other in a fluid enclosing relationship. As illustrated, such clamping means comprises elongate U-shaped members 24 which slide over walls 12 and 22 retaining the same in a box-like enclosure. Components 12, 22, 24 are suitably formed of a disposable plastic material such as polycarbonate, polyethylene, polypropylene or polyvinyl chloride or of a durable material such as a metal (e.g. aluminum) which would permit reuse of device 10 if desired.

As illustrated, membrane means 18 includes a porous reaction membrane with an externally visible upper surface.

The reaction membrane may be of any type capable of immobilizing reaction product of the reagents and sample component without adversely affecting the reaction, and permits passage of the remainder of the liquid sample or of a washing solution. Suitable membranes may be formed of any material capable of immobilizing the receptor reagent employed in the practice of the present invention, such as nylon, glass fibers, or other natural or synthetic materials which can be coupled directly or indirectly to the selected receptor. The porosity of the membrane preferably varies from about 0.2 to about 12 microns.

However, as a presently preferred embodiment, membrane means 18 comprises paper-backed nitrocellulose, or other types of nitrocellulose membranes with similar characteristics. This embodiment comprises a nitrocellulose membrane backed with porous paper similar to filter paper. A representative example is commercially available under the tradename BAC-T-KOTE by Schleicher and Schuell. This preferred membrane is substantially more durable than nitrocellulose alone and can be employed without any other support component. Also, it provides enhanced sensitivity to the reaction. Also, polyester supported nitrocellulose may be used such as supplied under the name NITROPLUS by Micron Separation, Inc.

As described below, in a typical system, a binding reagent is first immobilized on the membrane. The reagent reacts with and captures the predetermined target substance of the liquid sample to be assayed. Such reagent, typically an immunological protein such as an antibody or antigen, can be immobilized directly or indirectly onto such membranes, such as nitrocellulose, by either adsorption or by covalent bonding.

The depth or thickness of the membrane is selected so that an adequate amount of binding reagent can be immobilized to capture the sample component. However, the thickness should not be so great as to cause undue delay of the passage of the liquid sample through the membrane.

The absorbent body 20 of the present device can employ any of the known and conventionally employed absorbent materials which serve to draw liquid through a porous membrane, such as, for example, by capillary action. Useful known materials include cellulose acetate fibers, polyester, polyolefin or other such materials. It has also been found convenient to use layers of commercial available filter paper, or even toilet paper, which can be selected to provide sufficient volume to absorb the liquid employed during the assay of the present invention.

In one aspect of the device of the present invention, a flow-through system is provided for a Western blot analysis of a patient's serum for antibody. This has a number of significant advantages over conventional Western blot overlay techniques, not the least of which is the ability to perform the test in less than an hour, more specifically, in five to ten minutes or less. Furthermore, the test is easy to perform by lab technicians.

As illustrated, rim 16 projects from container top 10 towards reaction membrane 18 which is supported by absorbent body 20. When the unit is closed as illustrated in FIG. 3 and ready for the application of sample, rim 16 is pressed against the top surface of membrane 18 under sufficient compression to prevent any substantial leakage between the walls of rim 16 and the reaction membrane. An open space 26 is defined between the bottom of top wall 12 and the top of absorbent body 20 to the periphery of rim wall 16. This has been found to prevent leakage around rim 16, causing the liquid to flow through port 14 and the exposed area of membrane 18 rather than flowing along the top surface of membrane 18 and leaking through the contact points with rim 16. Preferably, rim 16 contacts membrane 18 along the length of the strip to the interior of the membrane side walls 18a. As illustrated, rim walls 16 provide a rim with a maximum thickness of less than about 5 mm and preferably less than about 3 mm at the contact point with membrane 18. Also, as illustrated, such contact point leaves a substantial portion of the top surface 18b of membrane 18 to the exterior of the contact point providing open space 26. As illustrated, such open space comprises a greater area than that portion of the upper membrane exposed to the port 14.

Figure 5:
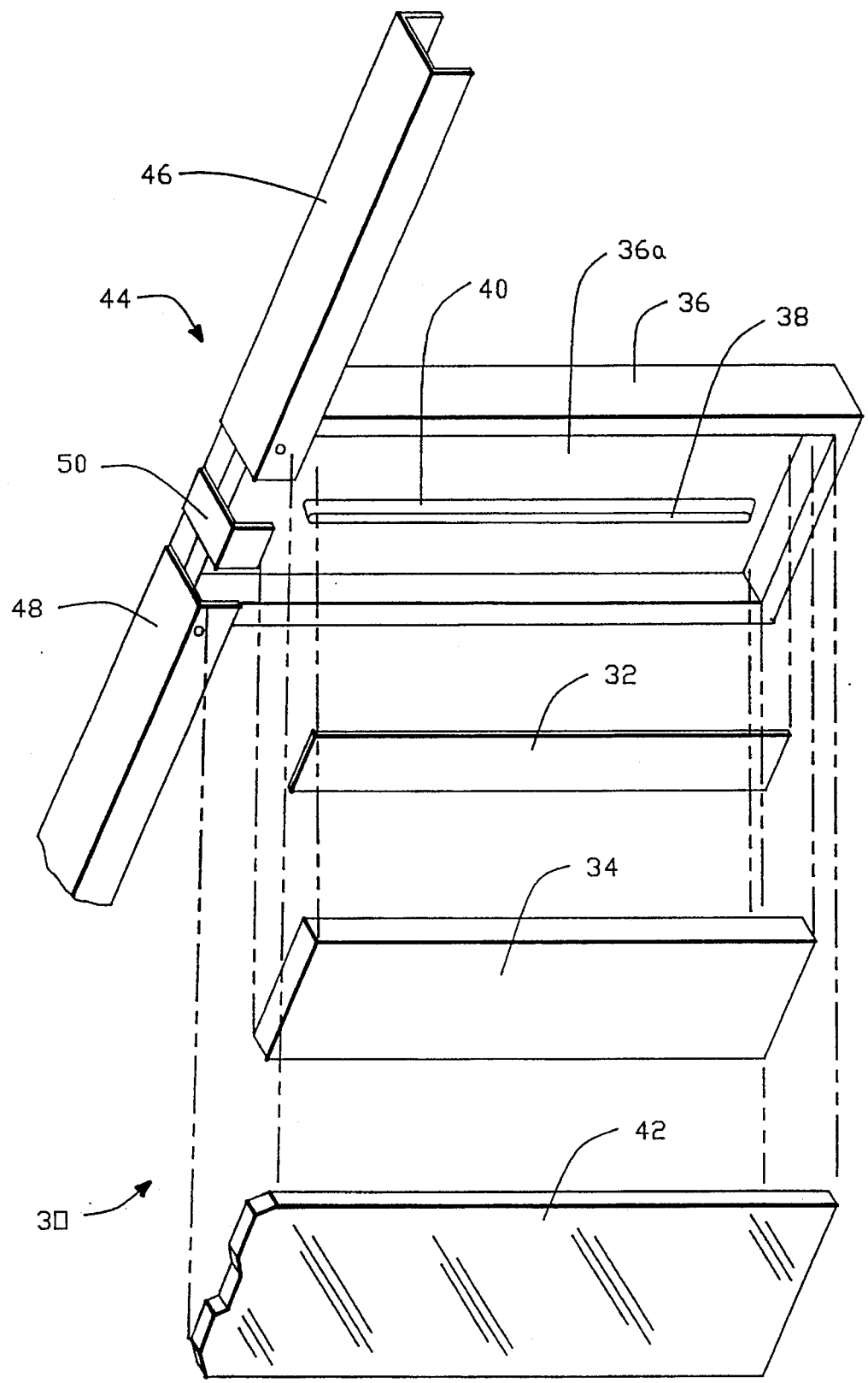
FIG. 5 is another embodiment of an assay device according to the invention.

An alternative form of the assay device of the present invention is illustrated in FIG. 5. That device is functionally equivalent to the device of FIGS. 1–4 but is more substantial in construction lending itself to many repeated uses. As the device, generally designated by the number 30, includes membrane 32 similar to membrane 18 and absorbent body 34 similar to absorbent body 20 of FIGS. 1–4. The top wall 36 is of rectangular shape and substantial thickness, suitably formed of a rigid plastic material. Top wall 36 defines a port 38 with a downwardly projecting rim 40 serving as sealing means similar to downwardly projecting rim 16 of FIGS. 1–4. Top wall 38 is undercut to define recess 36a in which absorbent material 34 is nested.

The device also includes a flat bottom wall 42 also suitably formed of rigid plastic. Absorbent material 34 rests on bottom wall 42.

Clamping means 44 is provided to form the unit into a generally fluid-tight rectangular box. Clamping means 44 include U-shaped walls 46 and 48 which are mounted for pivotal movement to top wall 36. Walls 46 and 48 retain the unit in a box-like configuration when closely adjacent to top wall 36 and bottom wall 42. An optional additional clamp 50 is also mounted to top wall 36 extending downwardly therefrom including an angle piece into which bottom wall 42 slides. In the illustrated embodiment, clamping means 44 is formed of metal while top and bottom walls 36 and 42 are formed of a durable plastic material.

The system is particularly applicable to an immunoassay wherein the sample component is one component of an immunological pair including antigens, antibodies, or haptens. The immunological pair includes two components which immunologically bind to each other. Specific immunological pairs include antigens and their antibodies (monoclonal antibodies or polyclonal antibodies), biologically functional haptens and their antibodies, enzymes and their substrates, hormones and their receptors, vitamins and their receptors, biotin and either avidin or an antibody to biotin, and lectin and its specific binding mono, di- or trisaccharide or glycoprotein.

For simplicity of description, the system will be described with respect to immunoassays using the antigen-antibody immunological pair. The liquid sample is biologically derived, (e.g., urine or serum) and the one reagent comprises a labelled antigen or antibody.

Referring first to a sandwich assay for the detection of antigen, the one reagent is a labelled antibody specific for the predetermined antigen in the sample. This system uses a second reagent, a capture antibody also specific for the predetermined antigen, immobilized on membrane disc 24a prior to addition of the liquid sample to the device. The techniques of immobilizing proteins such as monoclonal or polyclonal antibodies to solid surfaces such as membrane disc 24a without deactivation are well known. See e.g., Schuurs U.S. Pat. No. 3,551,555 and Hendry et al., J.

Immun. Methods, 35 1980, 285. For plastic materials such as nylon, such proteins may be immobilized by covalent bonding, e.g., as described in U.S. Pat. No. 3,720,760. The amount of protein immobilized per unit area of nylon is greater than that for nitrocellulose.

The labelled antibody or antigen described with respect to the sandwich assay may be any of the conventional types including radioactive, enzyme, or a metal complex label which are conjugated to the antibody. Formation of conjugates between such immunological substances and labels are well known, e.g., (a) radioactive labels—U.S. Pat. No. 3,646,346, Hunter et al., Nature 142 (1962), 945, (b) enzyme labels—U.S. Pat. Nos. 3,654,090, 3,791,931 and 3,817,838, Wilson et al., Immunoflourescense and Related Staining Techniques, Knapp., W. et al., Eds. L. Sevier-North Holland, Bio-Medical Press, New York-Amsterdam, 1978, pp. 215–224; (c) fluorescent quencher labels—U.S. Pat. No. 3,996,345; (d) radioactive labels—U.S. Pat. No. 4,062,733; (e) fluorescent or enzyme labels U.S. Pat. No. 4,067,959; (f) chemiluminescent labels—U.S. Pat. No. 4,104,029; (g) non-enzymatic catalyst label—U.S. Pat. No. 4,160,645; (h) enzyme pair labels—U.S. Pat. No. 4,233,402, chemically induced fluorescent labels—U.S. Pat. No. 4,720,450; and (i) enzyme non-ionic charge labels—U.S. Pat. No. 4,287,300. In addition, the labels disclosed in U.S. Pat. No. 4,366,241 may be employed. Also, colloidal gold labels are discussed in detail hereinafter.

Colloidal gold conjugates useful for probes such as cytochemical markers are well known for microscopy. See, e.g., *Scanning Electron Microscopy*, 1981, II, pp. 9–31, "Immunocytochemistry" Eds. Polak, J. N., et al., Bristol, London, Boston (1982) pp. 82–112, and *Journal of Neuroscience Methods*, 7(1983), pp.1–18. Colloidal gold particle markers are simple to use in comparison to other conventional markers. For example, they do not require instruments necessary for detection of other markers such as radioactive isotopes. Furthermore, unlike enzymes, they do not require the additional step of adding substrate. However, they have not been used extensively for commercial immunoassay kits, perhaps because of their low level of visibility using conventional techniques for mixing reactants. For example, the sensitivity of an assay using colloidal gold conjugates in a previous membrane system has been thought to be insufficient to provide the desired level of sensitivity. It has been found that by directing the flow of the liquid sample and reagents through the membrane, the sensitivity is so improved that colloidal gold particle conjugates are useful reagents for immunoassay kits without the need to use expensive microscopes.

If the sensitivity of the gold-immunological reagent conjugate is insufficient, even with the increase of the present system, a technique for enhancing the sensitivity of the gold complex may be employed such as disclosed in Holgate, C. S., et al., J. Histochem. Cytochem 31:938 (1983) and in Dancher, G, et al., J. Histochem. Cytochem 31:1394 (1983). This system is an "indirect" technique employing an immunological reagent, immunoglobulin, absorbed to colloidal gold. The gold particles are revealed by a silver precipitation reaction. In essence, the silver enhancement takes advantage of the catalytic effect of gold to catalyze the photographic physical developer process converting silver ion to silver metal. Suitable colloidal gold or gold sol particle size is from 3 nm to 150 nm. This immuno gold-silver staining method may have an enhanced sensitivity of up to 200-fold in comparison to the use of the gold particles without silver staining.

The present invention is also applicable to the competitive binding technique. In such system for the detection of antigen in a liquid sample, the corresponding member of the immunological pair, i.e., antibody is immobilized on to the membrane surface. Antigen labelled in the manner described above of the same immunological character as the antigen analyte to be detected in the sample is contacted with the immobilized antibody on the membrane. The immobilized antibody is in limited supply, and so a competition is set up between the antigen in the sample and the labelled antibody. Thus, the signal emitted from the label is inversely proportional to the amount of antigen in the sample. As with the sandwich assay, the competitive binding assay may be performed by reversing the roles of the antigen and antibody. In this instance, the immobilized member of the immunological pair is the antigen for the detection of antibody in the sample which competes with labelled antibody.

The immunoassays which have been described are the sandwich assay and the competitive binding assay. It should be understood that the system is also useful for other immunoassays such as, for example, described in U.S. Pat. No. 4,366,241.

The substances to be analyzed include a wide variety of biologically derived substances, e.g., proteins. The following is a list of some of these substances. (The listed substances also include immunologically reactive antibodies, and fractions of the substances).

Immunoglobulin
IgE
IgA
IgM
IgD
Microorganisms
*Aerobacter aerogenes*
Aerobic Spore-Forming Bacilli
    *Bacillus anthracis*
    *Bacillus subtilis*
    *Bacillus cereus*
Anaerobic Spore-forming Bacilli
    *Clostridium botulinum*
    *Clostridium tetani*
    *Clostridium perfringens*
Brucellae
    *Brucella melitensis*
    *Brucella abortus*
    *Brucella suis*
Chlamydia (unclassifiable parasites bacterial/viral)
Chlamydia agents (naming uncertain))
    *Chlamydia trachomatis*
Corynebacteria
    *Corynebacterium diptheriae*
*Escherichia coli*
Fungi
    *Cryptococcus neoformans*
    *Histoplasma capsulatum*
    *Coccidioides immitis*
    *Candida albicans*
    *Mucor corymbifer (absidia corymbifera)*
Hemophilus-Pordetella group
    *Hemophilus influenzae*
    *H. ducreyi*
    *H. hemophilus*
    *H. aegypticus*
    *H. parainfluenzae*

*Klebsiella pneumoniae*
Mycobacteria
  *Mycobacterium tuberculosis hominis*
  *Mycobacterium bovis*
  *Mycobacterium avium*
  *Mycobacterium leprae*
  *Mycobacterium paratuberculosis*
Mycoplasmas
  *Mycoplasma pneumoniae*
  *Mycoplasma hominis*
Neisseriae
  *Neisseria meningitidis*
  *Neisseria gonorrheae*
Other Pathogens
  *Listeria monocytogens*
Pasteurellae
  *Pasteurella pestis*
  *Pasteurella multocida*
Pneumococci
  *Diplococcus pneumoniae*
*Pseudomonas aeruginosa*
Rickettsiae (bacteria-like parasites)
  *Rickettsia prowazekii*
  *Rickettsia mooseri*
  *Rickettsia rickettsii*
  *Rickettsia conori*
  *Rickettsia australis*
  *Rickettsia tsutsugamushi*
  *Rickettsia burnetii*
*Salmonella choleraesus*
*Salmonella typhimurium*
*Salmonella typhosa*
*Shigella arabinotardo*
*Shigella boydii*
*Shigella dysenteriae*
*Shigella flexneri*
*Shigella schmitzii*
Shigella Sonnei
Staphylococci
  *Staphylococcus aureus*
  *Staphylococcus albus*
Streptococci
  *Streptococcus pyogenes*
  Groups B, C, D, F, G
The Spirochetes
  *Treponema pallidum*
  *Borrelia recurrentis*
  *Leptospira icterohemorrhagiae*
  *Leptospira canicola*
*Toxoplasma gondii*
Peptide and Protein Hormones
Corticotropin (ACTH) (adrenocorticotropic hormone)
Follicle-stimulating hormone
Luteinizing hormone (interstitial cell-stimulating hormone)
Parathyroid hormone
Prolactin
Chorionic Gonadotropin
Insulin
Glucagon
Relaxin
Somatropin
Triiodothyronine
Thyrocalcitonin
Thyroxine
Tissue Hormones
Angiotensin I and II
Bradykinin
Gastrin
Human placental lactogen
Secretin
Peptide Hormones
Oxytocin
Vasopressin
Viruses
Adinoviruses
Arboviruses
  Eastern Equine Eucephalitis Virus
  Western Equine Eucephalitis Virus
  Sindbis Virus
  Semliki Forest Virus
  St. Louis Encephalitis Virus
  California Encephalitis Virus
  Colorado Tick Fever Virus
  Yellow Fever Virus
  Dengue Virus
Hepatitis
  Hepatitis A Virus
  Hepatitis B Virus
Herpes Viruses
  Herpes simplex, Types I and II
  Varicella (Chicken pox)
  Cytomegalovirus
Myxoviruses
  Influenza (A, B, and C)
  Parainfluenza (1–4)
  Mumps virus
  Newcastle Disease Virus
  Measles Virus
  Canine Distemper Virus
  Respiratory Syncytial Virus
  Rubella Virus
Picornaviruses
  Poliovirus
  Coxsackievirus
  Echoviruses
  Rhinoviruses
Pox Viruses
  Vaccinia
  *Molluscum contagiosum*

The system is also applicable to other assay systems which are not categorized as immunoassays, e.g., the detection of unknown DNA sequences. For example, liquid sample containing the unknown DNA sequence is passed through the membrane and immobilize on the membrane as by contact with DNA previously immobilized on the membrane. Then, a labelled DNA probe passed in a liquid through the membrane. If hybridization occurs, the labelled DNA probe will be retained in detectible form on the membrane surface. This system is described in Polsky-Cynkin, R., et al., Clin. Chem. 31/9, 1438 (1985).

As mentioned above, in one assay, the immunological reagent is concentrated on at least one defined region on the membrane which appears as a dot but which actually extends through the membrane in a column of a diameter approximately equal to the dot. Referring to a sandwich or competitive binding techniques, this is accomplished by immobilizing the capture immunological reagent, e.g., antigen or antibody, only in such region by flowing the reagent to be immobilized through the membrane thickness. The reaction with the sample component and with the labelled reagent only occurs in that region.

The dot approach has certain advantages such as the performance of multiple simultaneous assays with a single device as described below. Also it provides a more distinctive end product signal since it is concentrated at a single region.

Another advantage of the dot approach is that it permits the simultaneous detection of multiple components in a sample. For example, with a single assay device, two different antibodies specific for predetermined different antigens can be immobilized on distinct spots on the membrane. The sample suspected of containing either one of the antigens is then contacted with the membrane and with labelled antibody specific for the two different membranes. A signal produced by the labels at one or the other of the dots indicates the presence or absence of one or both of the antigens. The dots may be distinguished from each other by their location or by an identification near each immobilized antibody dot. Thus, for example, if a color appears at the first dot but not the second, the first antigen but not the second antigen is present. If both dots appear, then both antigens are present, and if no dots appear, neither antigen is present. Alternatively, the label may be selected to produce different colors at each of the dots.

This system could be expanded to include the simultaneous detection of more than two components of the liquid sample by a corresponding number of immobilized immunological reagent on the membrane. In some instances, a first antibody is reactive with a particular subunit of a number of different antibodies. If a second antibody is specific for a subunit of one antigen only, such second antibody can be used as the immobilized antibody and a single labelled first antibody can be used as the universal labelled antibody for antigen of interest.

There are a number of advantages to using the device of the present invention. One advantage is the use of an elongate strip membrane and elongate port in registry with it. This adapts the apparatus to analysis of elongate separated proteins such as Western blots. Also, the use of spaced multiple dot blots permits linear variations in the concentrations of sample applied to the membrane merely be tilting the device and applying the sample to the upper end of the elongate port. The dots at the lower end receive higher concentrations than those at the top.

The standard protocols for the conventional immunoassays may be used in the present invention. For example, in a sandwich assay, the order of addition of the sample and labelled reagents may be simultaneous or sequential.

While monoclonal antibodies have known advantages and purity over polyclonal antibodies, either type of immunological reagent can be used in accordance with the present invention.

While the above system is described in terms of yes-no quantitative test, it should be understood that it is also suitable as semi-quantitative test using appropriate signals, such as colors, produced at different known concentrations of the component to be analyzed. Thus, for example, for the analysis of an antigen by a sandwich technique, the system can be run at progressive dilution to obtain an approximation of the color expected for a particular dilution. The unknown concentration of an antigen is compared to these colors to give an approximation of the concentration of antigen present in the sample.

One aspect of the present invention is the use of a flow-through device for the detection of antibody in an unknown sample, specifically serum, to a Western blot protein which had been previously immobilized or a membrane strip. For example, such Western blots of HIV lysate on recombinant protein are available commercially under the trademark (1) Biotech/DuPont HIV Western Blot Kit from E. I. DuPont DeNemours & Co., Inc., Wilmington, Del., (2) NOVOPATH™ strips from BioRad, Hercules, Calif., or (3) EPIblot-HIV Western Blot strips from Epitope, Inc., Beaverton, Oreg. The ability to use a flow-through device rather than an overlay leads to extraordinary savings in technician time and laboratory equipment. More specifically, a flow-through AIDS test can be performed in substantially less than one hour. More specifically less than ten minutes to as short a time as five minutes without the necessity of mechanical agitation used in an overlay procedure.

Another aspect of the invention is the discovery that the use of paper backed nitrocellulose has certain significant advantages. For example, in a test for antibody using an HIV Western blot, using colloidal gold conjugate, there is a substantial increase in the differential between the intensity of the positive and the background intensity (termed "net intensity").

Another aspect of the invention is the use of certain blocking reagents for such HIV Western blot significantly increases the net intensity. Specifically, the use of polyoxyethylene sorbitan monolaurate surfactant (TWEEN-20) at a concentration of 1% to 2% in solution dramatically increases such net intensity. An optimal amount of such polyoxyethylene sorbitan monolaurate surfactant (TWEEN-20) is on the order of 1.5%. The performance is further increased by the addition of a conventional non-interfering blocking protein such as bovine serum albumin (BSA), gelatin or casein to the blocking solution. Preferably the bovine serum albumin should be present in a concentration of about 0.5% to about 1.5% of the blocking solution.

A generalized procedure suitable for performing the method of the present invention to detect antibodies in a patient's serum against an HIV Western blot is as follows. First, a strip containing the HIV Western blot is placed into the device of FIGS. 1–4 on top of the absorbent material. Then the top wall is slid over the bottom wall so that rim 16 is pressed downwardly against the top surface of paper-backed nitrocellulose membrane 18. With the side walls of the bottom wall nested with the corresponding side walls of the top wall, U-shaped members 24 are used to retain the system in a liquid-tight, box-like enclosure.

Then, a blocking solution is applied to membrane 16. In this instance, the solution is applied to the upper surface of the membrane and is drawn through it under the influence of absorbent body 20. As set forth above, a particularly effective blocking solution is water-based and includes polyoxyethylene sorbitan monolaurate surfactant (TWEEN-20) and 1% to 2% of a non-interfering blocking protein such as BSA, casein or gelatin, at a concentration of about 0.5% to about 1.5%.

Then, the sample in the form of undiluted patient serum is applied to the top of the membrane. The sample flows through the membrane in about 15 to 30 seconds.

Then, the membrane is washed by passing washing solution in about 15 to 30 seconds. The washing solution may comprise the same solution as the blocking solution or any other known washing solution such as a low ionic strength buffer (e.g. less than 20 mM) or deionized water.

Then, a labelled conjugate reactive with the selected antibody in the patient's serum is added. In a preferred embodiment, the conjugate is of protein A with colloidal gold as a label. Alternatively, other labels may be employed for certain applications including enzyme or a radio active tag.

In a final step, another washing solution is applied to the membrane.

A specific example of the practice of the present invention are set forth in the following example by way of illustration.

EXAMPLE 1

This is a Western blot assay using the assay device of FIGS. 1–4.

HIV-1 viral lysate containing 800 micrograms/ml of viral proteins were mixed with an equal volume of 0.1M Tris-HCl buffer at pH 6.8 containing 2% SDS, 20% sucrose, and 0.01% bromophenol blue tracking dye. 40 microliter of this solution was loaded into a well of a Laemmeli SDS-polyacrylamide gel (10% acrylamide). The electrophoretic buffer system and running conditions were those of Laemmeli (Laemmeli, 1970 Nature vol. 227, p.680–685).

When the tracking dye reached the bottom of the gel, the electrophoretic run was terminated. The gel was removed and washed as described in the BIO-RAD Transblot manual. (BIO-RAD Laboratories, Inc., Hercules, Calif.) The protein in the gel was then transferred onto paper-backed nitrocellulose using the BIO-RAD transblot apparatus. The protocol and reagents used were those described in the Transblot operating manual. Electrophoretic blotting was carried out overnight at a constant voltage of 30 V.

The paper-backed nitrocellulose to which the blot was transferred was then placed between two absorbent filter papers and allowed to dry overnight. A strip from the sheet corresponding to the lane in which there were viral proteins was cut and mounted into the filtration device of FIGS. 1–4.

0.5 ml of a buffer containing 2% v/v polyoxyethylene sorbitan monolaurate surfactant (TWEEN-20) in 10 mM phosphate at pH 7.4 and 0.15M sodium chloride and 1% w/v bovine serum albumin was added and allowed to flow through the membrane to block off the remaining reactive sites. 0.3 ml of a seropositive human serum sample (control material from Biotech Research Laboratories, Rockville, Md.) was added and allowed to flow through the membrane. 0.3 ml of the same buffer used to wash the membrane was then added and allowed to flow through followed by 0.3 ml of deionized water. 0.4 ml of a solution of Protein-A colloidal gold was then added and allowed to flow through the membrane. (Protein-A colloidal gold with a particle size of 15 nm and at an optical density of 2.5 at wavelength 520 nm is available from E-Y Laboratories, Inc.). 0.4 ml of deionized water was then allowed to flow through the membrane as a final wash. The major bands required to indicate seropositivity was revealed as distinct red bands. The entire procedure, from time of adding the first buffer solution to the development of the bands, took five minutes.

What is claimed is:

1. A storage and reaction apparatus for use in assays for determining bindable target substances comprising:
    (a) a liquid-permeable, porous, elongate reaction membrane strip comprising an upper and lower surface, at least said upper surface comprising immobilized proteins capable of specifically binding to said target substances, said proteins being positioned on said strip so as to correspond to electrophoretically resolved proteins which have been transferred to said strip and which are capable of specifically binding to said target substances,
    (b) a body of absorbent material capable of absorbing liquid, said body having a surface located adjacent to the lower surface of the reaction membrane strip, and
    (c) a container means for said reaction membrane strip and said absorbent material comprising a top wall defining a fluid port in the form of an elongate slot adjacent said membrane strip and further comprising a fluid seal means peripherally disposed at said fluid port defining a seal between said container top wall and said reaction membrane strip.

2. The storage and reaction apparatus of claim 1 in which said fluid seal means comprises a continuous rim projecting from said container top wall towards said reaction membrane strip, said rim and said reaction membrane strip being in contact under sufficient compression to prevent leakage between said rim and reaction membrane strip.

3. The storage and reaction apparatus of claim 1 in which said rim is less than about 5 mm in width.

4. The storage and reaction apparatus of claim 1 in which said reaction membrane strip comprises nitrocellulose.

5. The storage and reaction apparatus of claim 1 in which said reaction membrane strip comprises a nitrocellulose membrane bonded to at least one liquid-permeable support material facing said absorbent material body.

6. The storage and reaction apparatus of claim 5 wherein said support material is paper, fiberglass or polyester.

7. The storage and reaction apparatus of claim 1 in which said reaction membrane strip rests on said absorbent material body and is removable from said container means.

8. The storage and reaction apparatus of claim 1 in which said container top wall is detachably mounted to said container means.

9. A storage and reaction apparatus for use in assays for determining a bindable target substance in a liquid sample suspected of containing said target substance, comprising:
    (a) a liquid-permeable, porous, elongate reaction membrane strip comprising an upper surface, a lower surface, and side walls, at least said upper surface comprising an immobilized receptor capable of specifically binding to said target substance,
    (b) a body of absorbent material capable of absorbing liquid, said body having a surface located adjacent to the lower surface of the reaction membrane strip, and
    (c) a container means for said reaction membrane strip and said absorbent material comprising a top wall defining an elongate slot fluid port adjacent said reaction membrane strip and further comprising a fluid seal peripherally disposed at said fluid port defining a seal between said container top wall and said reaction membrane strip, said fluid seal comprises a continuous rim projecting from said container top wall towards said reaction membrane strip, said rim and said reaction membrane strip being in contact under sufficient compression to prevent leakage between said rim and said reaction membrane strip, said rim having an outer wall projecting to an area of said reaction membrane strip interior of said side walls thereby forming an open area on the top of the strip outside the rim and free of contact with the rim.

10. An assay for determining bindable target antibodies in a liquid sample suspected of containing said antibodies, employing as an assay device an apparatus comprising:
    (a) a liquid-permeable, porous, elongate reaction membrane strip comprising an upper and lower surface, at least said upper surface comprising immobilized proteins capable of specifically binding to said target antibodies, said proteins being positioned on said strip so as to correspond to electrophoretically resolved proteins which have been transferred to said strip and which are capable of specifically binding to said target antibodies, (b) a body of absorbent material capable of absorbing liquid, said body having a surface located adjacent to the lower surface of the reaction membrane strip, (c) a container means for said reaction membrane strip and said absorbent material comprising a top wall defining a fluid port in the form of an elongate slot adjacent said reaction membrane strip and further comprising a fluid seal means peripherally disposed at said fluid port defining a seal between said container top wall and said reaction membrane strip, said assay comprising applying said liquid sample to the upper surface of said permeable reaction membrane strip whereby said antibodies, if present in said liquid sample, specifically bind to said immobilized proteins and unbound sample permeates through said fluid port and the membrane lower surface into said absorbent body; applying a visible labelled substance capable of directly or indirectly specifically binding to said antibodies to the upper surface of said permeable reaction membrane strip whereby said visible labelled substance specifically binds any bound target antibodies and unbound visible labelled substance permeates through said fluid port and the membrane lower surface into said absorbent body; and, thereafter determining any visible labelled substance specifically bound to said upper surface as an indication of the presence or amount of said target antibodies in said liquid sample.

11. The assay of claim 10 in which said fluid seal means comprises a continuous rim projecting from said container top wall towards said reaction membrane strip, said rim and said reaction membrane strip being in contact under sufficient compression to prevent leakage between said rim and reaction membrane strip.

12. The assay of claim 10 in which said reaction membrane strip comprises nitrocellulose.

13. The assay of claim 10 in which said reaction membrane strip comprises a nitrocellulose membrane bonded to at least one liquid-permeable support material facing said absorbent material body.

14. The assay of claim 10 in which the label of said visible labelled substance comprises colloidal gold.

15. The assay of claim 10 performed in less than ten minutes.

16. The assay of claim 10 in which said proteins comprise HIV proteins.

17. The assay of claim 16 in which said HIV proteins comprise recombinant HIV proteins.

18. The assay of claim 16 in which said HIV proteins comprise virus lysate.

19. The assay of claim 10 in which a blocking agent is added to the reaction membrane strip prior to addition of said visible labelled substance, said blocking agent comprising between about 1% and about 2% polyoxyethylene sorbitan monolaurate surfactant.

20. The assay of claim 19 in which said blocking agent further comprises a non-interfering blocking protein serum albumin.

21. An assay for determining bindable target antibody in a liquid sample suspected of containing said antibody, employing as an assay device an apparatus comprising a liquid-permeable, porous, elongate reaction membrane strip comprising an upper and lower surface, at least said upper surface comprising immobilized protein antigen capable of specifically binding to said target antibody, a body of absorbent material capable of absorbing said sample, said body comprising a surface located adjacent to the lower surface of the reaction membrane strip, and a container means for said reaction membrane strip and said absorbent material comprising a top wall defining a port adjacent said reaction membrane strip and further comprising a fluid seal means peripherally disposed at said fluid port defining a seal between said container top wall and said reaction membrane strip, said assay comprising:

(a) applying a blocking solution to said reaction membrane strip, said blocking solution comprising between about 1% and about 2% polyoxyethylene sorbitan monolaurate surfactant and between about 0.5% and about 1.5% immunologically non-reactive protein, (b) applying said liquid sample to the upper surface of said reaction membrane strip whereby said antibody, if present in said liquid sample, specifically binds to said immobilized proteins and unbound sample permeates through said fluid port and the membrane lower surface into said absorbent body; applying a visible labelled substance capable of directly or indirectly specifically binding to said antibodies to the upper surface of said permeable reaction membrane strip whereby said visible labelled substance specifically binds any bound target antibody and unbound visible labelled substance permeates through said fluid port and the membrane lower surface into said absorbent body; and, (c) thereafter determining any visible labelled substance specifically bound to said upper surface as an indication of the presence or amount of said target antibody in said liquid sample.

22. The assay of claim 21 in which said non-interfering protein comprises bovine serum albumin.

23. The assay of claim 21 in which said reaction membrane strip comprises nitrocellulose.

\* \* \* \* \*